United States Patent
Heidenreich et al.

(10) Patent No.: US 9,927,500 B2
(45) Date of Patent: Mar. 27, 2018

(54) DEVICE FOR GENERATING A MAGNETIC FIELD PROFILE WHICH MEETS THE REQUIREMENTS FOR MPI AND FOR MRI

(71) Applicant: BRUKER BIOSPIN MRI GMBH, Ettlingen (DE)

(72) Inventors: Michael Heidenreich, Karlsruhe (DE); Jochen Franke, Karlsruhe (DE); Volker Niemann, Ispringen (DE); Rainer Pietig, Malsch (DE)

(73) Assignee: Bruker BioSpin MRI GmbH, Ettlingen (DE)

( * ) Notice: Subject to any disclaimer, the term of this patent is extended or adjusted under 35 U.S.C. 154(b) by 579 days.

(21) Appl. No.: 14/427,647

(22) PCT Filed: Aug. 16, 2013

(86) PCT No.: PCT/EP2013/067149
§ 371 (c)(1),
(2) Date: Mar. 12, 2015

(87) PCT Pub. No.: WO2014/040822
PCT Pub. Date: Mar. 20, 2014

(65) Prior Publication Data
US 2015/0285875 A1  Oct. 8, 2015

(30) Foreign Application Priority Data
Sep. 14, 2012  (DE) .................. 10 2012 216 357

(51) Int. Cl.
*G01V 3/00* (2006.01)
*G01R 33/12* (2006.01)
(Continued)

(52) U.S. Cl.
CPC ........ *G01R 33/1276* (2013.01); *A61B 5/0035* (2013.01); *A61B 5/055* (2013.01);
(Continued)

(58) Field of Classification Search
USPC ......................................... 324/319
See application file for complete search history.

(56) References Cited

U.S. PATENT DOCUMENTS

| 5,814,993 A | 9/1998 | Frese |
| 2003/0085703 A1 | 5/2003 | Gleich |

(Continued)

FOREIGN PATENT DOCUMENTS

| JP | 2009 195614 | 9/2009 |
| WO | WO 2012/077015 | 6/2012 |

OTHER PUBLICATIONS

J. Weizenecker et al., "Three-dimensional real-time in vivo magnetic particle imaging", Phys. Med. Biol. 54 (2009) L1-L10.
(Continued)

*Primary Examiner* — Rodney Fuller
(74) *Attorney, Agent, or Firm* — Paul Vincent (57) ABSTRACT

Device for alternating examination of a measurement object (103) by means of MPI and MRI within a magnetic system is characterized in that the magnetic system has a specified magnetic field profile, which is not temporally variable during the alternating examination, and both magnetic field generating elements (101,102; 201,202; 801a,801b,811,812) generate a magnetic field portion, in the first examination region (104) and in the second examination region (105), which is essential for the MRI operation and for the MPI operation, and in that there is a transport apparatus (106) by means of which the measurement object can be moved out of the first examination region and into the second examination region and/or vice versa. The total space requirement for both modalities is thus reduced and the complexity of an integrally designed hybrid system is minimized.

11 Claims, 12 Drawing Sheets

(51) Int. Cl.
    *A61B 5/05*     (2006.01)
    *A61B 5/055*     (2006.01)
    *G01R 33/48*     (2006.01)
    *A61B 5/00*     (2006.01)
    *G01R 33/3815*     (2006.01)
    *G01R 33/383*     (2006.01)
    *G01R 33/563*     (2006.01)

(52) U.S. Cl.
    CPC .......... *A61B 5/0515* (2013.01); *G01R 33/383* (2013.01); *G01R 33/3815* (2013.01); *G01R 33/4808* (2013.01); *G01R 33/5635* (2013.01)

(56) References Cited

U.S. PATENT DOCUMENTS

| | | | | |
|---|---|---|---|---|
| 2008/0303523 | A1* | 12/2008 | Overweg | G01R 33/385 324/319 |
| 2009/0195249 | A1 | 8/2009 | DeMeester | |
| 2010/0277263 | A1* | 11/2010 | Schnur | G01R 33/3815 335/216 |
| 2011/0234217 | A1* | 9/2011 | Timinger | A61B 5/05 324/244 |
| 2013/0102472 | A1* | 4/2013 | Iwasa | G01R 33/035 505/162 |
| 2016/0111192 | A1* | 4/2016 | Suzara | H01F 6/06 335/301 |

OTHER PUBLICATIONS

Timo F. Sattel et al., "Single-sided device for magnetic particle imaging", J. Phys. D. Appl. Phys. 42 (2009) (5pp).

Bernhard Gleich et al., "Tomographic imaging using the nonlinear response of magnetic particles", Nature vol. 435/Jun. 30, 2005, doi: 10.1038/nature 03808.

T. Knopp et al., "Field-free line formation in a magnetic field", J. Phys. A: Math. Theor. 43(2010)012002 (9pp).

J. Franke et al., "First hybrid MPI-MRI imaging system as integrated design for mice and rats: Description of the instrumentation setup",Magnetic particle imaging (IWMPI), 2013, Intern. Workshop on, IEEE, Mar. 23, 2013, Pa. 1.

J. Weizenecker et al., "A simulation study on the resolution and sensitivity of magnetic particle imaging", Phys. Med. Biol. 52 (2007) 6363-6374, doi: 10.1088/0031-9155/52/21/001.

T. Knopp et al., "Trajectory analysis for magnetic particle imaging", Phys. Med. Biol. 54 (2009) 385-397, doi: 10.1088/0031-9155/54/2/014.

* cited by examiner

DEVICE FOR GENERATING A MAGNETIC FIELD PROFILE WHICH MEETS THE REQUIREMENTS FOR MPI AND FOR MRI

This application is the national stage of PCT/EP2013/067149, filed Aug. 16, 2013 and claims Paris convention priority from DE 10 2012 216 357.3, filed Sep. 14, 2012, the entire disclosures of which are hereby incorporated by reference.

BACKGROUND OF THE INVENTION

The invention relates to a device for alternating examination of a measurement object by means of MPI (="Magnetic Particle Imaging") and MRI (="Magnetic Resonance Imaging") within a magnetic system comprised of at least two magnetic field generating elements, wherein the magnetic system has a first examination region for the MRI operation, in which a homogenous magnetic field is generated, and wherein the magnetic system has a second examination region for the MPI operation, in which a spatially strongly varying magnetic field profile is generated, the field vectors thereof being different at all spatial points with regard to direction and/or amount and comprising one spatial point of zero field magnitude.

Such a device is known from reference [3] (Weizenecker et al., 2009).

In recent decades, several tomographic imaging methods have been invented, including, for example, computer tomography (CT) by Hounsfield in 1969, magnetic resonance tomography (MRI) by Lauterbur and Mansfield in 1973, or positron emission tomography (PET) by Ter-Pogossian and Phelps in 1975. With the constant development of hardware, sequence and/or reconstruction algorithms, imaging methods are assuming an ever more important role in medical diagnosis today. By combining individual imaging methods into so-called hybrid systems (for example, PET-CT in clinical use since 2001 and MRI-PET in clinical use since 2010), it has been possible to further improve the diagnostic accuracy of imaging methods. A common feature of all hybrid systems is that complementary information from the individual modalities is combined synergistically and/or overlaid graphically. So, for example, CT data from a PET-CT hybrid system are used for morphological information and for attenuation correction of the PET data.

In 2001, a further tomographic imaging method called magnetic particle imaging (MPI) was invented by Gleich and Weizenäcker (DE10151778A1). This recent and fast developing volumetric imaging method is used to detect the spatial distribution of applied superparamagnetic nanoparticles (SPIO). This method offers spatial as well as high temporal resolution performance (see references [1-3]).

The fundamental principle of MPI is based on the excitation of nanoparticles using a magnetic field that changes over time, the so-called "drive field" (DF), with an excitation frequency f0. The non-linear magnetization curve of the SPIOs produce harmonics of F0 as the particle response, which are detected by means of receiver coils and are used for image reconstruction. Because tissue produces a negligibly small non-linear response to the excitation frequency f0, this method offers a high contrast by acquisition of the particle response only. Spatial encoding is based on the effect that the particle magnetization becomes saturated above a certain magnetic field strength. As a result of magnetic excitation at frequency f0, the magnetization of the saturated SPIOs only changes minimally and therefore its contribution to the particle response is non existent or minimal. In order to exploit this saturation effect, a static magnetic field gradient—the so-called "selection field" (SF)—with a field-free point (FFP) is generated. Starting out from the FFP, the magnetic field strength increases in all spatial directions.

Such a magnetic field profile can be produced, for example, with permanent magnets with opposed magnetization directions or by using a Maxwell electromagnetic coil pair. Only particles in the direct vicinity of the FFP are excited by the saturation effect and thus contribute to the response of the particles. The extent of the FFP and thus the sensitivity of the MPI method is dependent on the magnetic field strength with which the particles reach saturation, and on the gradient strength of the SF, with which the magnetic field increases starting from the FFP (see references [4, 5]). To allow volumetric imaging, the FFP is controlled relative to the object under examination by, for example, the superposition of additional magnetic fields and/or the mechanical movement of the object under examination.

The MPI quantitative method with its high level of sensitivity and high temporal resolution offers promising non-invasive application possibilities in the field of molecular and medical imaging such as, for example, cell tracking or cancer diagnosis and in the field of cardiovascular diagnosis and blood vessel imaging. Unlike other imaging methods such as, for example, CT and MRI, MPI image data sets thus acquired still produce a relatively low spatial resolution in the millimeter range. This limited resolution is due to the currently available nanoparticles and the magnetic field gradients that are technically feasible. Moreover, data having high sensitivity exclusively with respect to the applied nanoparticles can provide information about the quantitative distribution of these nanoparticles, although this contains little morphological information. This makes it extremely difficult to uniquely assign the measured distribution of the particles to their morphological location of origin.

Other volumetric imaging methods such as, for example, the MRI method, which has been in clinical use for a long time, are very suitable for acquiring high-resolution morphological information. The MRI technique is based on a highly homogeneous magnetic field and electromagnetic alternating fields in the radio-frequency range, with which certain atomic nuclei in the object under examination can be excited (see reference [6]). The excited atomic nuclei themselves emit alternating electromagnetic fields, which induce electric signals in the receiver coil. By using multiple magnetic field gradients, the signal is spatially encoded and can be reconstructed by suitable algorithms. MRI not only enables the acquisition of high-resolution anatomical information with varied soft tissue contrasts in the sub-millimeter range, but also offers further differentiated techniques, which provide access to many physiological parameters, such as water diffusion or permeability. If MR spectroscopic imaging is used, metabolic and biochemical processes can also be represented spatially. Unlike MPI, the MRI technique is a relatively insensitive and slow imaging method with acquisition times in the seconds to minutes range.

The unique characteristics of both volumetric imaging modalities make MPI and MRI largely complementary in terms of the information they contain. Superior diagnostic validity can be achieved by combining both methods and making synergetic use of their properties—the high sensitivity and temporal resolution of the MPI technique and the varied soft tissue contrasts and therefore excellent morphological information of the MRI technique. Superposition/fusion of both complementary image data sets has so far only been implemented using two separate or independent modalities of MPI and MRI (see reference [3]) as no integrated combined device (hybrid device) of these two modalities is yet available anywhere in the world.

However, using two separate modalities poses many difficulties. These include the co-registration of both data sets with different reference coordinates, which is hampered by the largely unavoidable shifting and deformation caused by repositioning and/or transportation of the object under examination from one modality to the other. Intermodality transportation also reduces the direct correlation between the two data sets in time. Further logistical problems result, for example, in studies with small animals, which require the laboratory animal to be continuously anesthetized. The provision of two standalone modalities also means high costs and space requirements. A combination of both modalities in an integrated hybrid device was disclosed in JP-2009195614-A2, although the hybrid device described therein has two different modes (MRI and MPI), which are implemented by switching partial coil systems on and off.

The object of this invention is to improve a device having the characteristics defined above in a low-cost manner and by using simple technical means in such a way that the difficulties described above in combining the two modalities into an integrated hybrid device are reduced or avoided, wherein the total space requirement for both modalities is reduced and the complexity of the integrally designed hybrid system is minimized and switching between the two modes with respect to the magnetic field profile is no longer necessary.

SUMMARY OF THE INVENTION

This object is achieved with a device according to the independent claim, which is characterized in that the magnetic system has a specified magnetic field profile, which is not temporally variable during the alternating examination, and both magnetic field generating elements generate a magnetic field portion, in the first examination region and in the second examination region, which is essential for the MRI operation and for the MPI operation, and in that there is a transport apparatus by means of which the measurement object can be moved out of the first examination region and into the second examination region and/or vice versa.

This invention proposes magnetic system configurations, which meet the needs of both MRI and MPI imaging. The two separate examination regions allow optimum exploitation of each measurement volume. The MPI part of the device can, for example, be retrofitted to an existing MRI system.

In the case of an integrally designed hybrid device comprising an MRI and an MPI modality, the magnetic system configuration must produce a magnetic field profile that contains both a homogeneous field region for MR imaging as well as a field region with a spatial field gradient including a field zero crossing. In MPI technology, the field region that contains the field of zero magnitude is called a field-free point (FFP).

Further variants as well as advantageous characteristics and embodiments of the invention are described in the dependent claims.

Embodiments are particularly advantageous in which both magnetic field generating elements of the magnetic system are disposed in a single housing. A hybrid device consisting of an MRI and an MPI modality differs from two separate and/or standalone modalities by the fact that the system has an integrated design, i.e. at least one magnetic field generating element significantly contributes to the magnetic field profile of the examination region of both modalities (see FIG. 1). Moreover, integrally designed hybrid devices also permit shared use of additional components such as, for example, the control software and partial components of the transmitter and/or receiver circuits.

Figure 1:
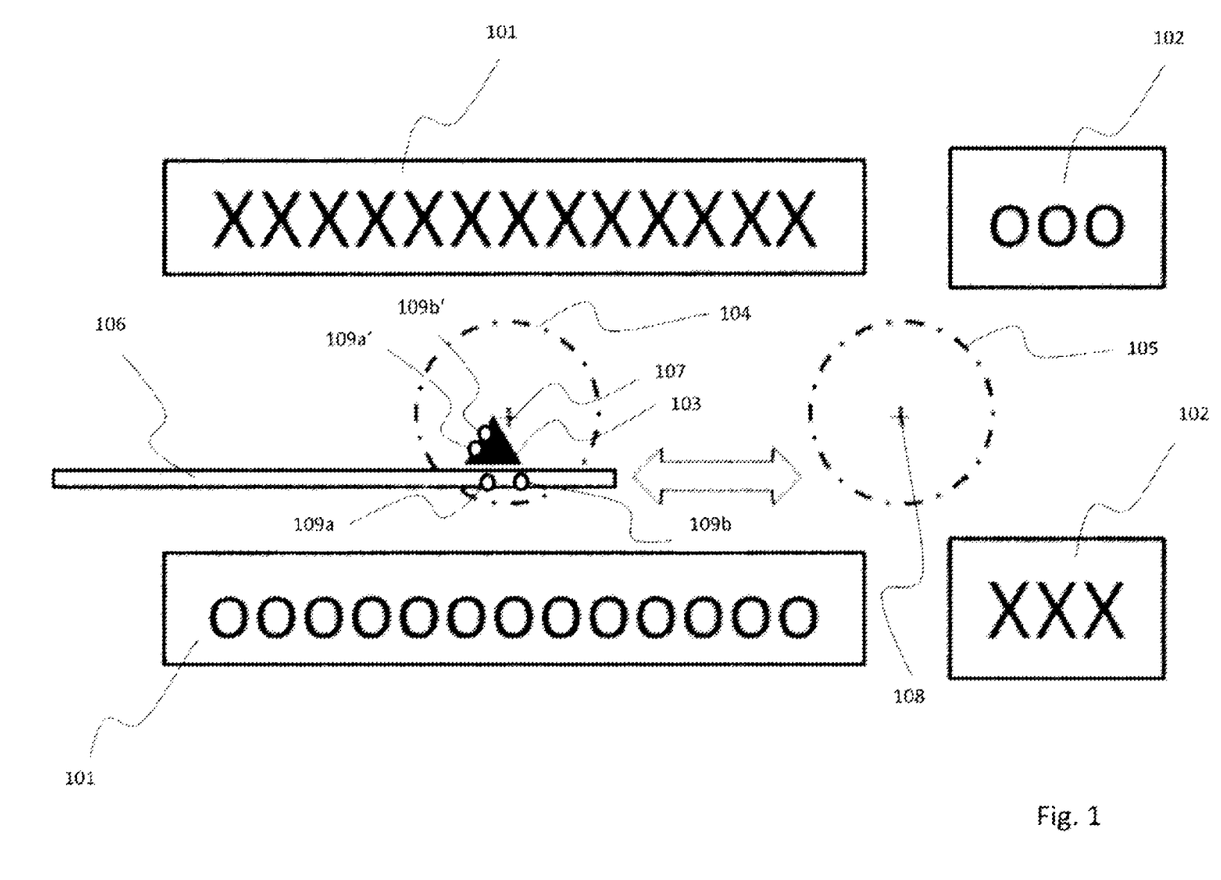
FIG. 1 Schematic representation of a section through the magnetic field generating elements 101, 102 of an integrated MRI-MPI hybrid system, wherein the embodiment is represented as resistive and/or superconducting electromagnetic systems. The examination locations for MRI 104 and MPI 105, the object under examination 103, and the transport unit 106 are represented schematically here.

In the configurations described here, the measurement object can be transported between both examination regions by means of a transport unit (schematically depicted in FIG. 1).

In order to generate magnetic fields, superconducting electromagnetic coil systems, resistive electromagnetic coil systems, permanent magnet systems and/or a combination of these can be used.

A specially preferred class of embodiments for the practical application of the inventive device is characterized by a magnetic system comprising a superconducting electromagnetic coil system, which is disposed in a cryostat and is superconductively short-circuited during operation.

Alternatively or additionally, in another class of embodiments, the magnetic system can comprise a resistive electromagnetic coil system, in which all of its partial coils are electrically connected in series.

If one or more superconducting electromagnetic coil systems are used as a field generator, the configuration must be implemented in conjunction with a single cryostat. A strong static magnetic field B0 and a strong magnetic field gradient G can be generated with superconducting electromagnets.

In the MRI, the strength of the static magnetic field has a direct effect on the signal-to-noise ratio (SNR), which increases approximately proportionally to B0. In MPI technology, the spatial resolution performance for a particular tracer is proportional to 1/G. As the magnetic field gradient increases, the extent of the FFP, in which the nanoparticles are not in saturation and therefore contribute to the reception signal, decreases. Compared with a design with resistive electromagnets, a design with superconducting electromagnetics combined with a cryostat drastically reduces the energy required during operation as well as the cooling requirements and therefore the space requirement in the equipment room.

Superconducting electromagnets also offer good long-term stability due to their constant temperature control in the cryostat. Coaxially disposed magnetic systems permit simple calculation and implementation of the necessary magnetic field homogeneity and magnetic field gradient.

In the case of symmetrically and coaxially disposed magnetic field systems, the force applied is minimal/symmetrical and makes design easier.

In one design of the field generator with a resistive electromagnetic coil system, in which all the partial coils are connected in series and disposed coaxially, the strength of the static magnetic field and the strength of the magnetic field gradient can be freely selected within certain limits by defining the coil current. This is of particular interest for the MPI mode because the extent of the field of view (FOV) at a constant DF amplitude is proportional to 1/G.

Moreover, in resistive electromagnetic coil systems, it is possible to deactivate the static field/gradient field when the system is not in use, which reduces the risks associated with strong magnetic fields. Furthermore, deactivating the static magnetic field permits optimum use of new approaches in system calibration using the "system calibration unit" in MPI imaging (see reference [7]).

The use of permanent magnet systems permits the generation of moderate static magnetic fields and strong magnetic field gradients. The cooling requirements of such systems are low compared with resistive systems because they are only required to control the temperature of the magnetic field generating elements and thus to stabilize their magnetic properties. The use of permanent magnet systems moreover reduces the total energy consumption of the system during operation. The overall system (including the equipment room) can also be implemented in a compact way.

Marking devices are helpful for positioning the object under examination in the center of the examination region in question.

Furthermore, if parts of these marking devices are fitted to one or more spatial points on the transport unit or patient table and/or on the measurement object itself and constituted as a proton marker, these spatial points can be localized in the MRI image. Additionally defined spatial points can be provided with MPI markers for spatial point localization in the MPI data. The information from the various spatial points of each modality that is gained in this way can be used for stable and precise co-registration of both image data sets, thus allowing a high level of precision of the fused images.

Optimum use of all MRI components (such as, for example, the MR transmitter and/or receiver coil) demands that the homogenous magnetic center (=isocenter) of the field generator coincide with the magnetic center of the other MRI components or with the MRI examination region.

The same applies to the MPI components (such as, for example, the drive-field coils), for which the zero crossing of the field amount (the FFP) of the field generator coincides with the magnetic center of the other MPI components and/or with the MPI examination region.

To minimize interference/noise between the MRI components and the MPI components, both examination regions must be shielded with respect to radio-frequency radiation and low-frequency radiation.

In preferred embodiments of the invention, the stray field of the magnetic system is reduced in its spatial extent by active and/or passive shielding.

To retrofit already installed MRI devices to an integrated MRI-MPI hybrid device, magnetic field generating elements (resistive, superconducting, or permanent) can be constituted as an attachment/extension. An MPI retrofit of existing MRI devices would be a low-cost alternative to the installation of a new hybrid device, with minimal installation effort due to shared use of existing components and the surrounding infrastructure.

Implementing a zero crossing of the magnetic field gradient as a field-free line (FFL) instead of an FFP offers alternative/new MPI acquisition approaches with a potentially higher sensitivity and shorter acquisition time (see reference [7]).

Further advantages result from the description and the drawings. Moreover, according to the invention, the features stated above and further below can be used singly or together in any combination. The embodiments shown and described are not intended to be an exhaustive list, rather are examples to explain the invention. The invention is shown in the drawings and is explained in more detail by way of embodiments. The figures show:

DESCRIPTION OF THE PREFERRED EMBODIMENT

Example 1: Superconducting Electromagnetic Coil System

Figure 2:
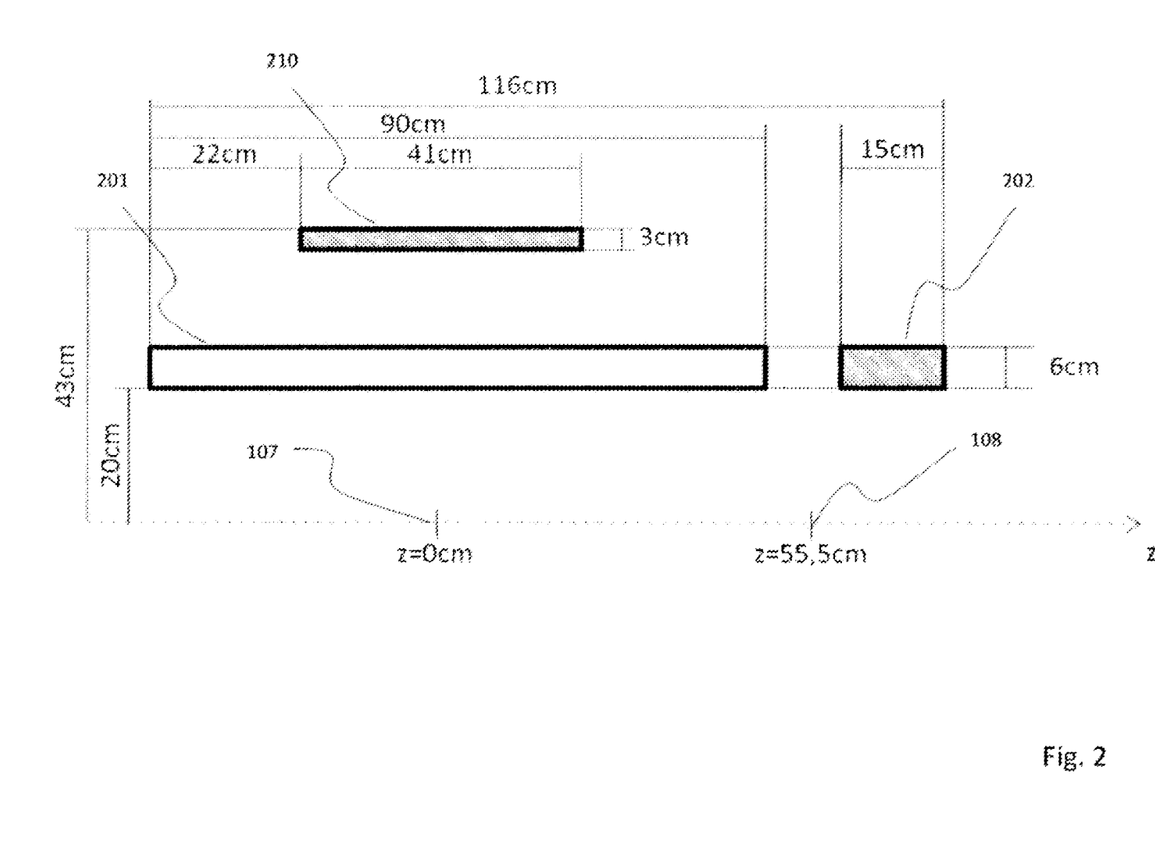
FIG. 2 Schematic section through three axially disposed superconducting magnetic field generating elements 201, 202, 210 of example 1, with rotational symmetry about a z axis. Coil element 201 and coil element 202 in a Maxwell configuration are used to generate a magnetic field gradient with a B0 field zero crossing of an FFP 108. Coil element 210 is used for the active shielding of the magnetic field towards the outside and causes homogenization of the B0 field inside.
Figure 3:
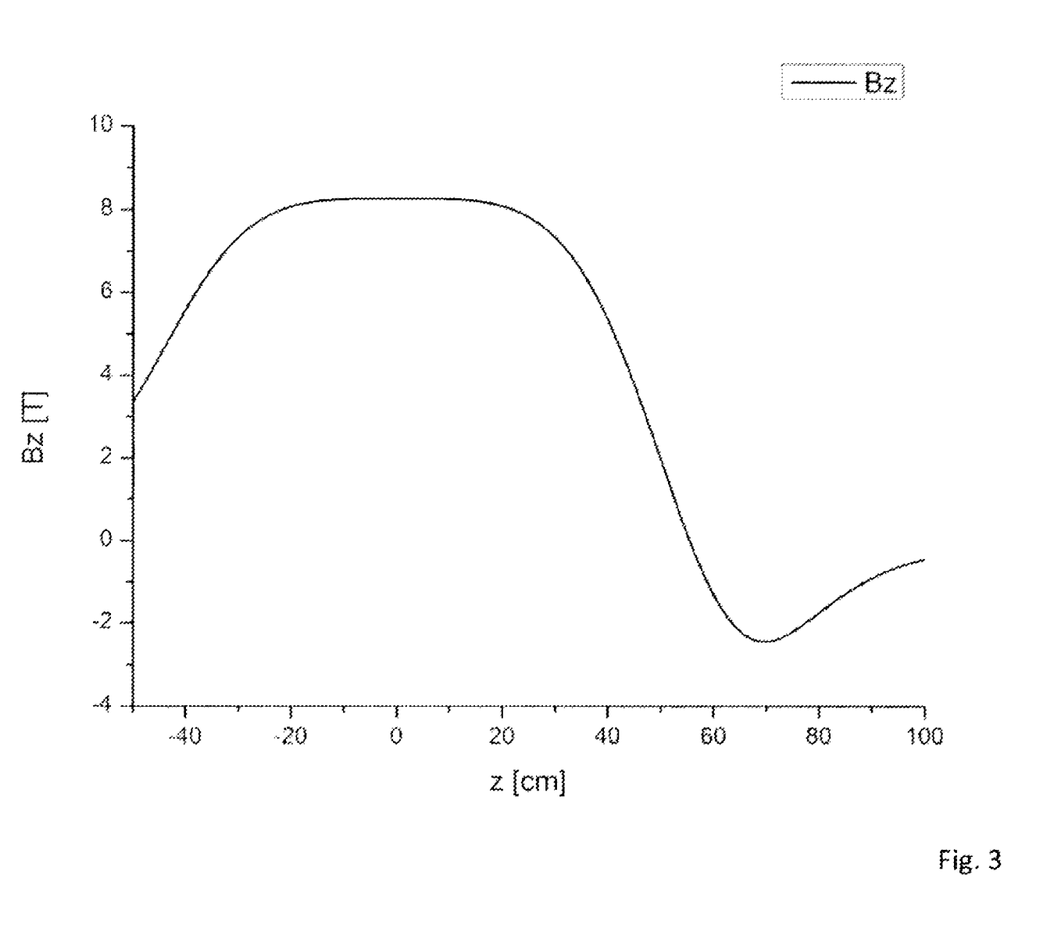
FIG. 3 Simulation of the overall axial magnetic field profile at r=0 cm of example 1 shown in FIG. 2. The first region designates the examination region, which satisfies the MRI requirements, i.e. a high static and homogenous magnetic field, wherein z=0 denotes the isocenter. The second region designates the examination region, which satisfies the MPI requirements, i.e. a strong magnetic field gradient with B0 zero crossing, which represents the FFP.
Figure 4:
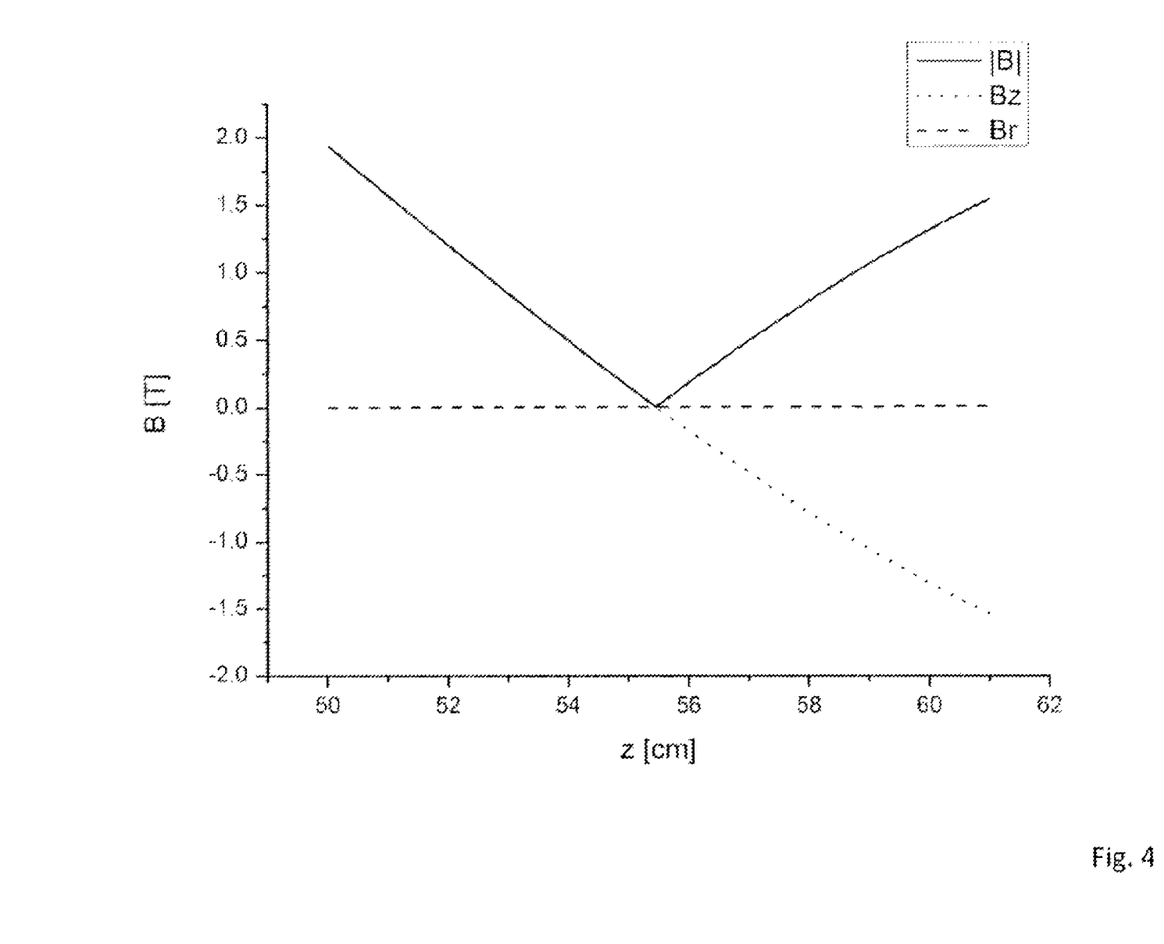
FIG. 4 Simulation of the axial magnetic field profile of the example 1, where r=0 cm in the region of the FFP of the MPI examination region.
Figure 5:
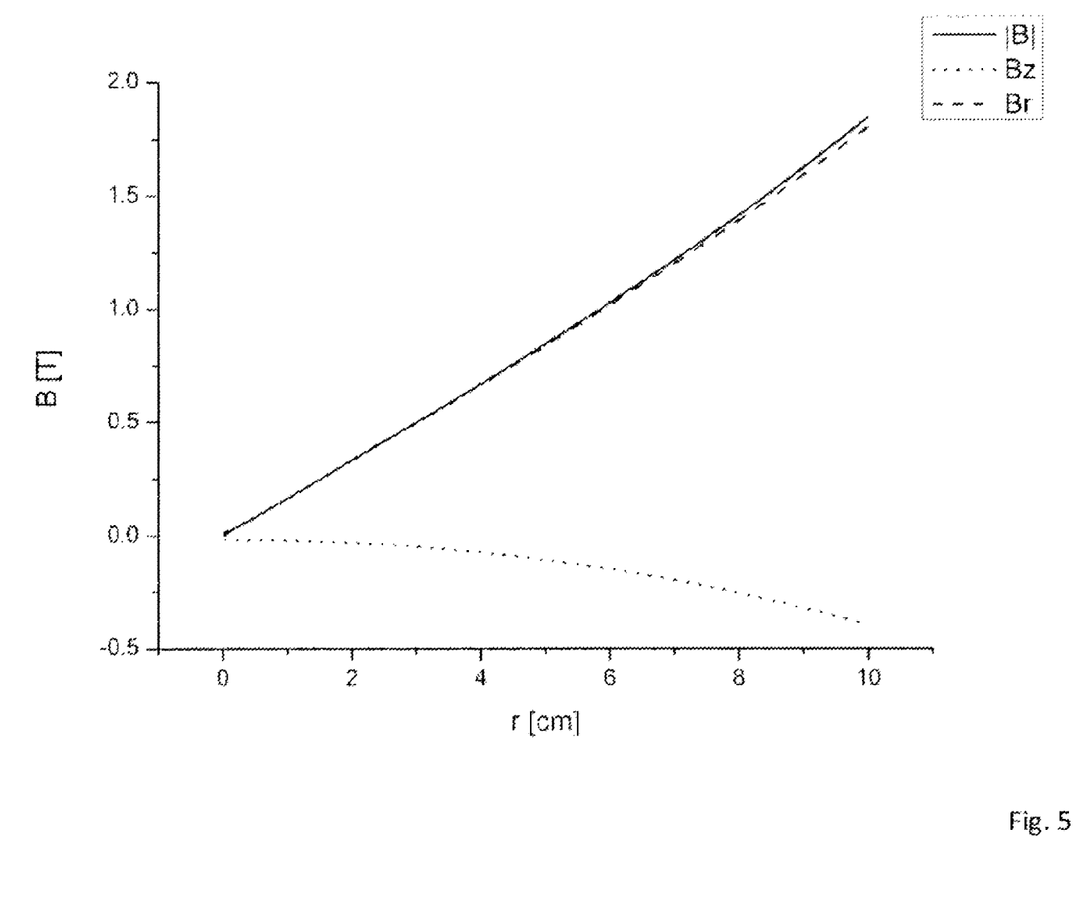
FIG. 5 Simulation of the rotationally symmetrical magnetic field profile of the example 1 in the axial direction where z=55.5 cm (FFP) of the MPI examination region.
Figure 6:
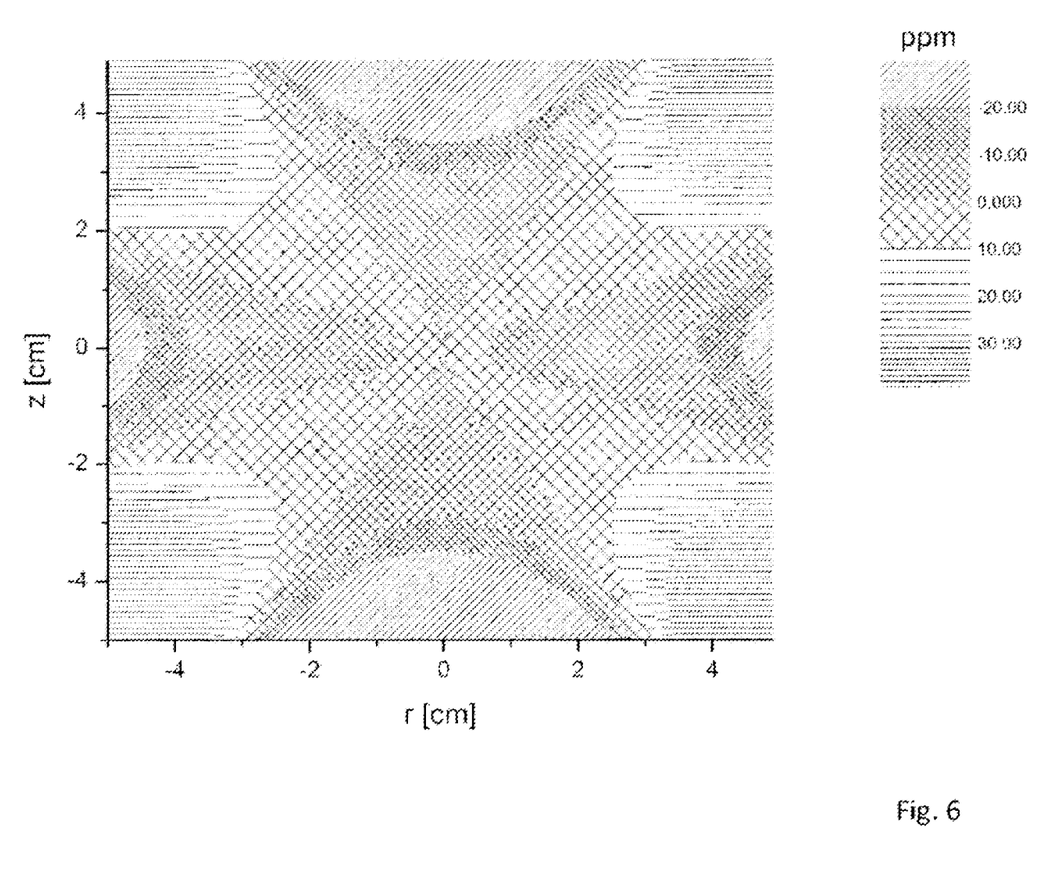
FIG. 6 Simulated magnetic field homogeneity of the example 1 in the region of the isocenter 107 of the MRI examination region.
Figure 7:
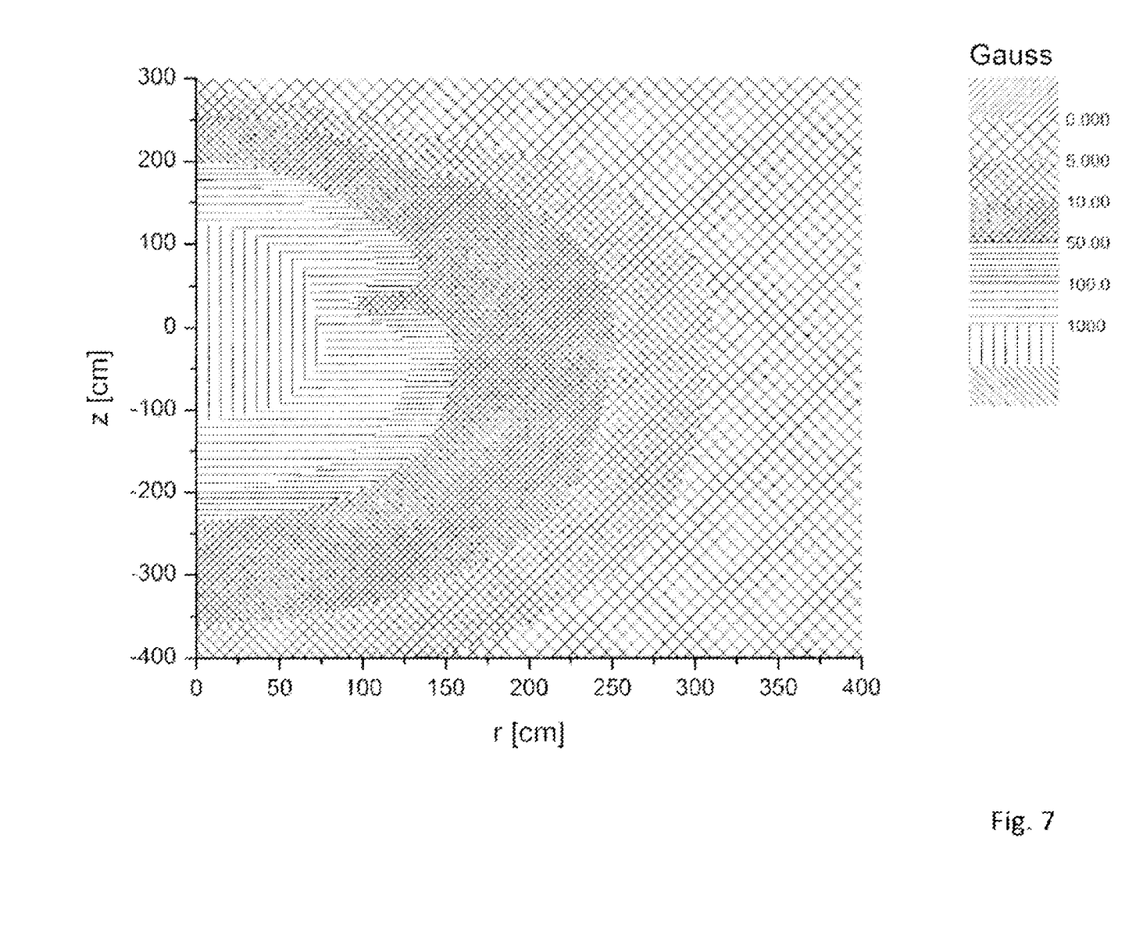
FIG. 7 Simulated stray field of the example 1.

Example 1 only uses superconducting magnetic field generating elements 201, 202, 210 (see FIG. 2), which generate the magnetic field profile, which is not temporally variable, in FIG. 3. This integrated configuration of the hybrid system consists of three solenoid partial coil elements (total weight of coils approx. 120 kg) disposed coaxially in a cryostat (4.2K) and wound from NbTi conductors, shown in FIG. 2. The main coil 201 generates the static magnetic field B0, which is homogenized internally by coil 201 (see FIG. 6) and which is shielded towards the outside (see FIG. 7). The current flow directions of coils 201 and 210 are antiparallel. Coil 202, which is axially displaced with respect to the main coil and operated in an anti-Helmholtz configuration, increases the inherent magnetic field gradient of main coil 201 and generates an FFP 108 (see FIGS. 5 and 6). The configuration produces a homogenous static magnetic field B0 of approx. 8 T in MRI examination region 104 and a magnetic field gradient of approx. 35 T/m in MPI examination region 105.

Example 2: Permanent Magnet

Figure 8:
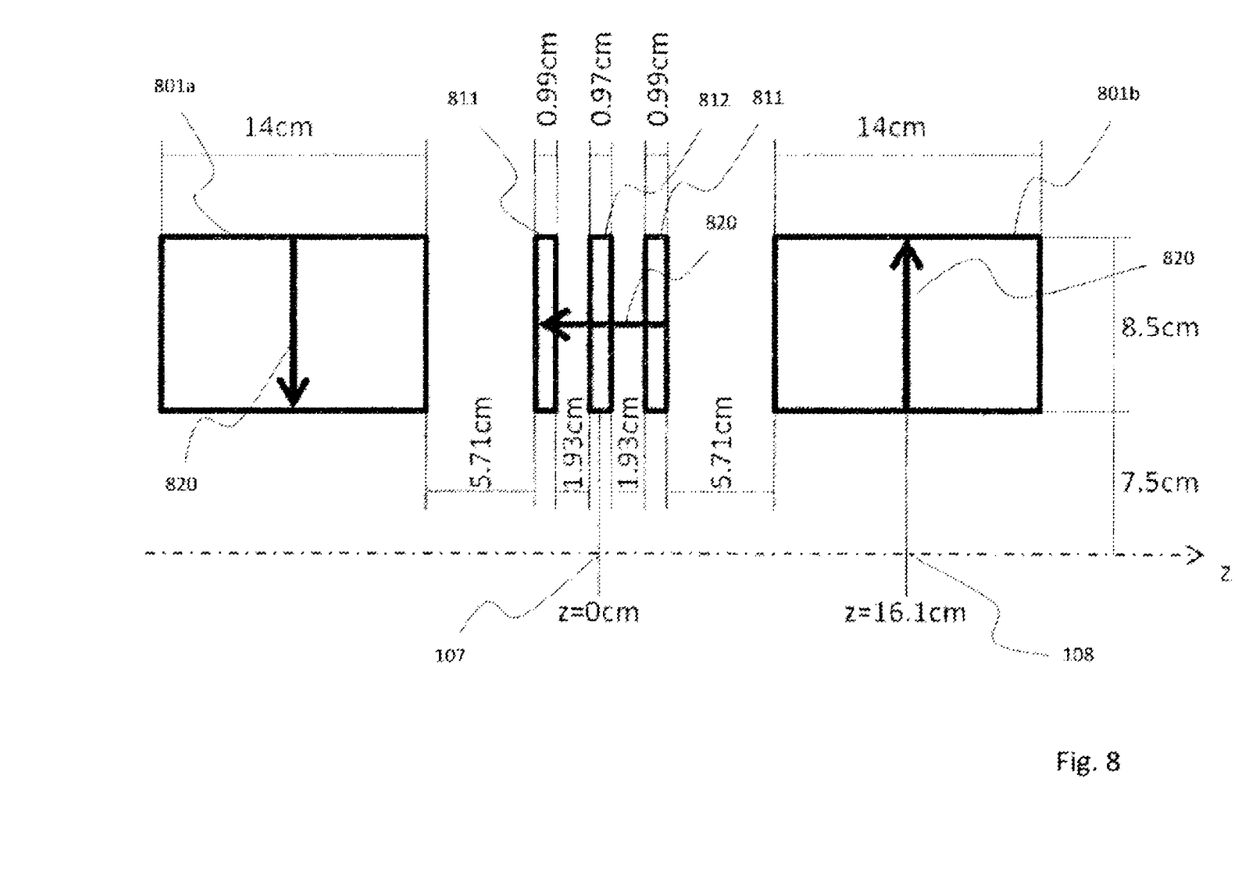
FIG. 8 Sectional view through the upper part of the five axially disposed permanent magnets, which serve as magnetic field generating elements of the example 2. The two outer inversely radially magnetized neodymium-iron-boron (NdFeB) rings with a magnetic remanence of Br=1.4 T each generate a magnetic field gradient with a B0 zero crossing to provide two FFPs as well as a homogenous field portion B0. The central axially magnetized ring elements serve to homogenize the static magnetic field. The arrows indicate the magnetization vector of the NdFeB rings.
Figure 9:
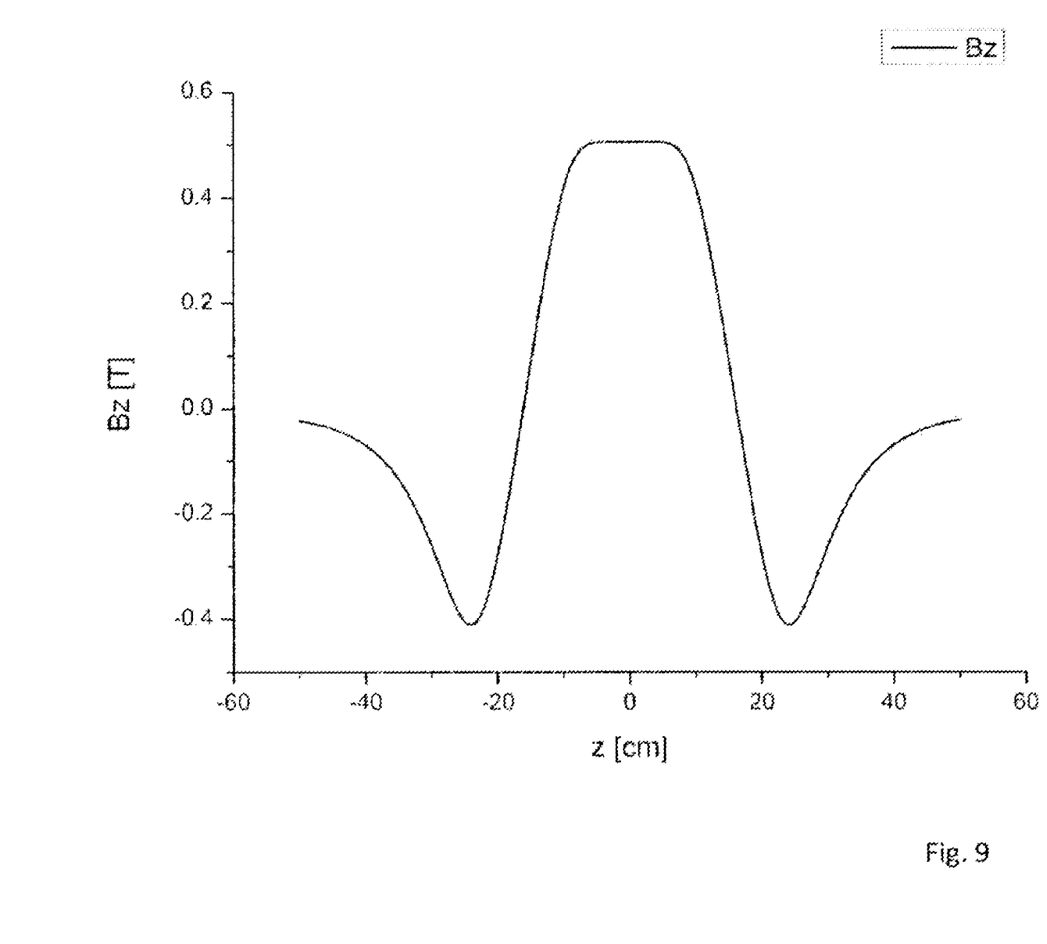
FIG. 9 Simulation of the whole axial magnetic field profile at r=0 cm of example 2 shown in FIG. 8. The central region designates the examination region, which satisfies the MRI requirements, i.e. a high static and homogenous magnetic field, wherein the isocenter is at z=0. The region around the zero crossing designates the examination region, which satisfies the MPI requirements, i.e. a strong magnetic field gradient with B0 zero crossing, which represents the FFP.
Figure 10:
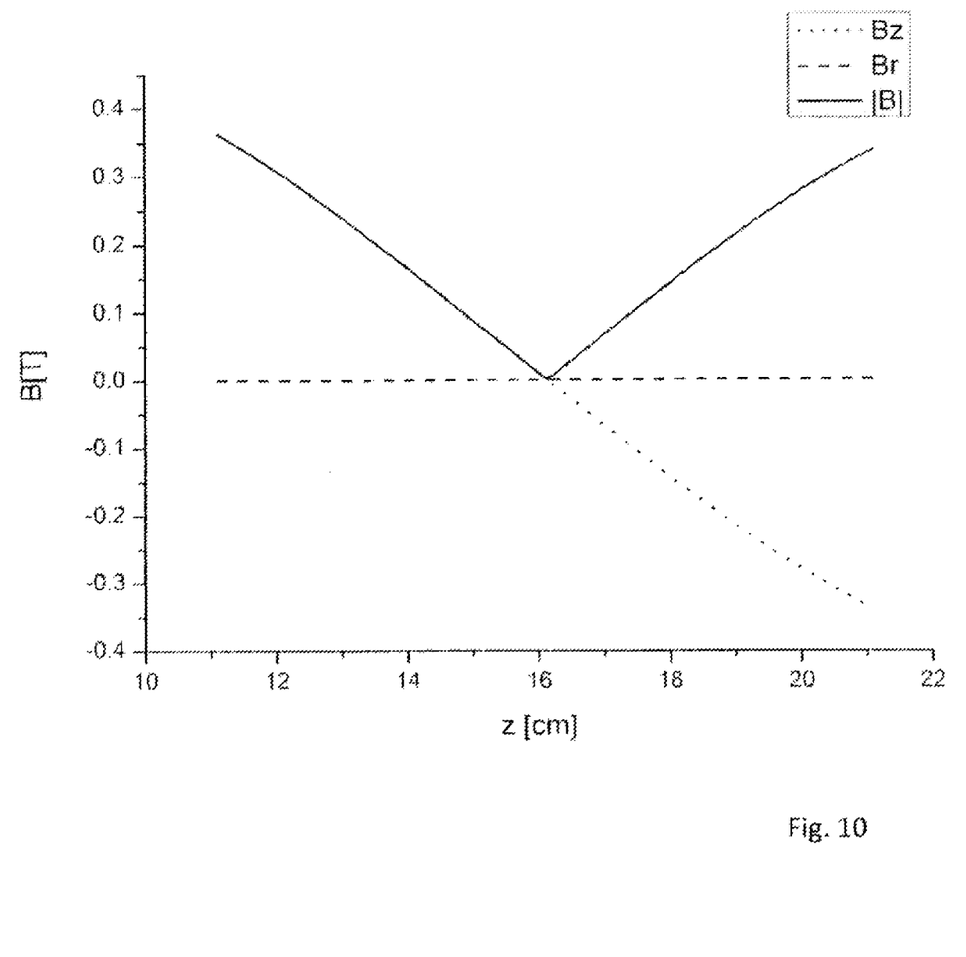
FIG. 10 Simulation of the axial magnetic field profile of the example 2 where r=0 cm in the region of the FFP (z=16.1 cm) of the MPI examination region.
Figure 11:
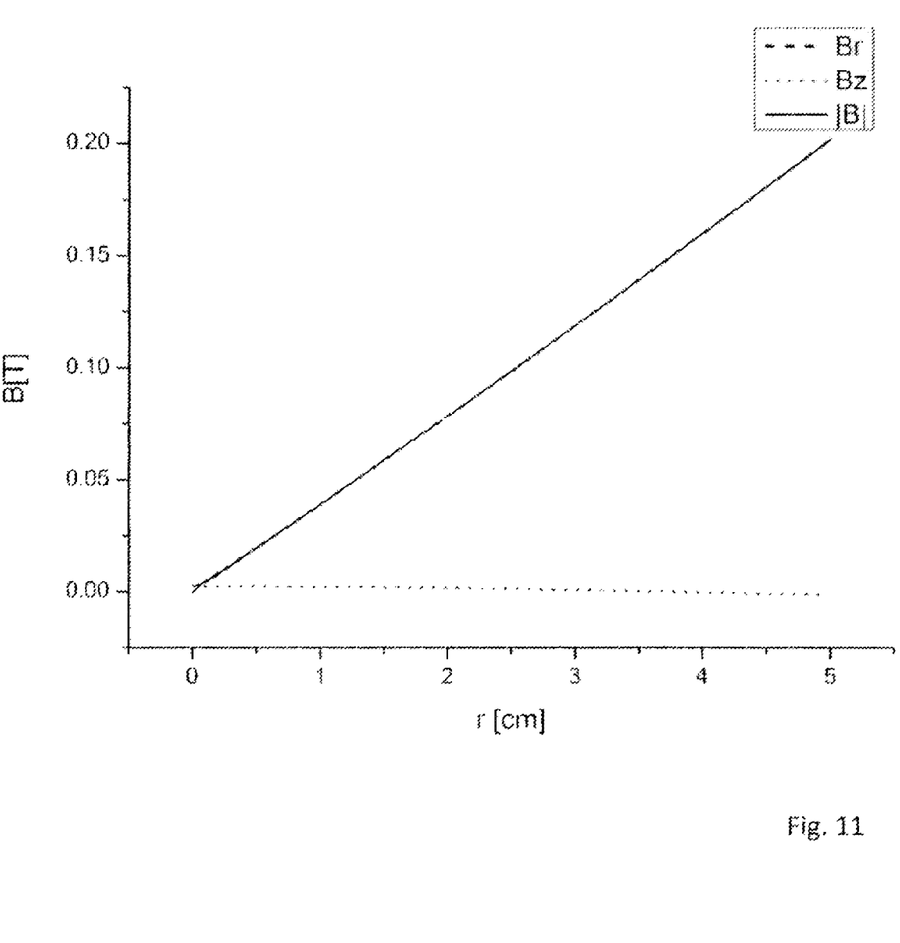
FIG. 11 Simulation of the rotationally symmetrical magnetic field profile of the example 2 in the axial direction where z=16.1 cm (FFP) of the MPI examination region.
Figure 12:
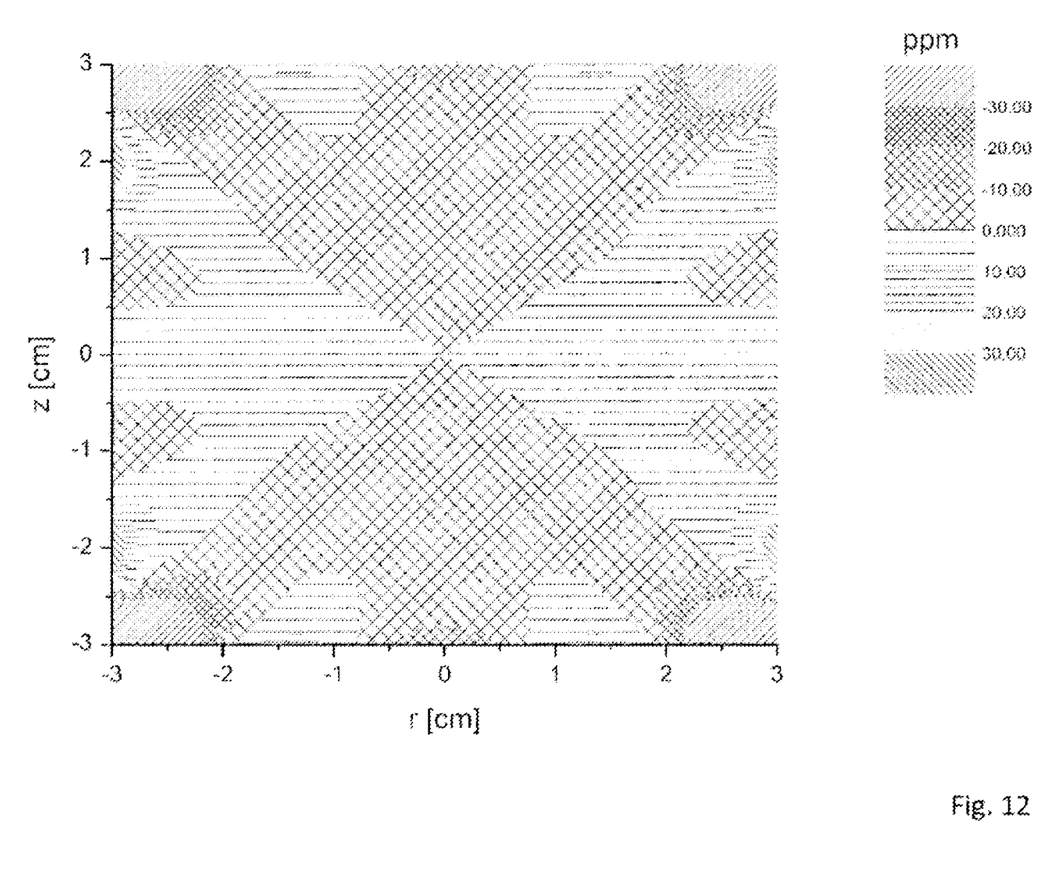
FIG. 12 Simulated magnetic field homogeneity of the example 2 in the region of the isocenter of the MRI examination region.

Example 2 only uses permanent magnetic field generating elements 801a, 801b, 811, 812, which generate the magnetic field profile, which is not temporally variable, in FIG. 9. This symmetrical and integrated configuration of the hybrid system consists of a total of 5 coaxially disposed magnetized rings 801a, 801b, 811, 812 (see FIG. 8) made from neodymium-iron-boron (NdFeB) and with a magnetized remanence of Br=1.4 T (total weight of the magnetic system approx. 150 kg). The outer main magnet rings 801a, 801b, which generate the homogenous magnetic field region as well as the magnetic field gradient (see FIG. 10-11) are, in practice, manufactured from segments in order to achieve a radial magnetization direction. Axially magnetized ring magnets can be used to increase the magnetic field homogeneity of the B0 field in the central region. In this example, only three axially magnetized ring magnets 811, 812 are used, which is a compromise between complexity of the system and the field homogeneity achieved with it (see FIG. 12). The symmetrical configuration in the Z direction dispenses with the uneven field orders (field distortion components) and makes homogenization of the magnetic field easier in the central region. This configuration produces a static magnetic field B0 of approx. 0.5 T in the MRI examination region 104 and a magnetic field gradient of approx. 7.7 T/m in the MPI examination region 105. To further increase the magnetic field gradient, the main magnet rings 801a, 801b can be manufactured conically (i.e. the length of the main magnet rings in the Z direction is longer at the inner radius than at the outer radius) rather than cylindrically as in this example.

LIST OF REFERENCE SYMBOLS

101 Solenoid main coil
102 Solenoid coil operated in an anti-Helmholtz configuration with respect to the main coil
103 Measurement object
104 MRI examination region
105 MPI examination region
106 Transport apparatus
107 MRI isocenter
108 Field-free point (MPI center)
109a MRI marker (proton marker) on the patient table
109a MRI marker (proton marker) on the measurement object
109b MPI marker on the patient table
109b MPI marker on the measurement object
201 Superconducting solenoid main coil
202 Superconducting solenoid coil operated in an anti-Helmholtz configuration with respect to the main coil
210 Superconducting homogenization and shielding coil operated in an anti-Helmholtz configuration with respect to the main coil
801a Radially magnetized main magnet ring
801b Main magnet ring magnetized radially in opposite direction to 801a
811 Axially magnetized ring magnets for homogenization of the B0 field
812 Axially magnetized ring magnet for homogenization of the B0 field
820 Magnetization direction

REFERENCES

[1] Gleich B and Weizenecker J 2005 Tomographic imaging using the nonlinear response of magnetic particles Nature 435 1214-7
[2] Sattel T F, Knopp T, Biederer S, Gleich B, Weizenecker J, Borgert J and Buzug T M 2009 Single-sided device for magnetic particle imaging. J. Phys. D: Appl. Phys. 42 1-5
[3] Weizenecker J, Gleich B, Rahmer J, Dahnke H and Borgert J 2009 Three-dimensional real-time in vivo magnetic particle imaging. Phys. Med. Biol. 54 L1-L10
[4] Weizenecker J, Borgert J and Gleich B 2007 A simulation study on the resolution and sensitivity of magnetic particle imaging. Phys. Med. Biol. 52 6363-74
[5] Knopp T, Biederer S, Sattel T, Weizenecker J, Gleich B, Borgert J and Buzug T M 2009 Trajectory analysis for magnetic particle imaging. Phys. Med. Biol. 54 385-97
[6] Vlaadingerbroek M T and den Boer J A 2003 Magnetic Resonance Imaging. Springer-Verlag 3rd Edition
[7] Magnetic Particle Imaging—A Novl SPIO Nanoparticle Imaging Technique. Springer Springer Proceedings in Physics

We claim:
1. A device for alternating examination of a measurement object by means of MPI (="Magnetic Particle Imaging") and MRI (="Magnetic Resonance Imaging") within a magnetic system, the device comprising:
a first magnetic field generating element, said first magnetic field generating element comprising a main solenoid coil;
a second magnetic field generating element, wherein said first magnetic field generating element and said second magnetic field generating element comprise electromagnetic coils disposed coaxially along a z-axis, said second magnetic field generating element comprising a second solenoid coil which is displaced axially in a direction of a z-axis relative to said main solenoid coil and which is operated in anti-Helmholtz configuration with respect to said main solenoid coil;
magnetic system elements defining a first examination region for MRI operation, in which a homogenous magnetic field is generated;
magnetic system elements defining a second examination region for MPI operation, in which a spatially strongly varying magnetic field profile is generated, field vectors thereof being different at all spatial points with regard to direction and/or amount and having one spatial point of zero field magnitude;
a transport apparatus by means of which the measurement object can be moved out of said first examination region and into said second examination region and/or vice versa; and a third magnetic field generating element for improving a homogeneity of a magnetic field in said first examination region by compensating for field gradients generated by said second magnetic field generating element and/or for shielding the magnet system, wherein said third magnetic field generating element is disposed radially outside of said first magnetic field generating element and axially symmetric relative to an isocenter, which, during operation of the device, has a homogeneous magnetic field radially within the magnet system at an axial position z=0 and which coincides with a magnetic center of said first examination region.

2. The device of claim 1, wherein a conceptual middle plane of said solenoidal first magnetic field generating element, which is perpendicular to and intersects the z-axis, is displaced away from the z=0 axial position towards said second magnetic field generating element.

3. The device of claim 1, wherein at least one of said first and said second magnetic field generating elements is a permanent magnet.

4. The device of claim 1, wherein the magnetic system comprises an electromagnetic coil system, in which all partial coils thereof are electrically connected in series.

5. The device of claim 1, wherein the magnetic system comprises a superconducting electromagnetic coil system, which is disposed in a cryostat and is superconductively short-circuited during operation.

6. The device of claim 1, wherein said first magnetic field generating element and said second magnetic field generating element are disposed in a single housing.

7. The device of claim 1, further comprising a marking device having at least one proton marker to highlight one or more spatial points of said first examination region on an MRI image and/or at least one MPI marker to highlight one or more spatial points of said second examination region on an MPI image.

8. The device of claim 7, wherein at least parts of said marking device are mounted on a table for the measurement object or on a patient to be examined with the device.

9. The device of claim 1, wherein said first examination region and said second examination region are shielded with respect to both radio-frequency radiation and low-frequency radiation.

10. The device of claim 1, wherein a zero crossing of a field gradient is a field-free line.

11. The device of claim 1, wherein a stray field of the magnetic system is reduced in spatial extent by an active and/or passive shielding.

* * * * *